United States Patent [19]

Scholl et al.

[11] Patent Number: 5,130,492

[45] Date of Patent: Jul. 14, 1992

[54] PROCESS FOR THE PRODUCTION OF SQUARIC ACID

[75] Inventors: Thomas Scholl, Visp; Barry Jackson, Glis, both of Switzerland

[73] Assignee: Lonza Ltd., Gampel/Valais, Switzerland

[21] Appl. No.: 651,982

[22] Filed: Feb. 7, 1991

[30] Foreign Application Priority Data

Feb. 12, 1990 [CH] Switzerland .............................. 439/90

[51] Int. Cl.$^5$ ................................................ C07C 45/43
[52] U.S. Cl. ..................................... 568/348; 568/346; 568/381
[58] Field of Search ........................ 568/346, 381, 348

[56] References Cited

U.S. PATENT DOCUMENTS

| | | | |
|---|---|---|---|
| 3,288,854 | 11/1966 | Martin | 568/381 |
| 3,456,010 | 7/1969 | Megson et al. | 260/567.6 |
| 4,159,387 | 6/1979 | Bellus | 568/381 |

FOREIGN PATENT DOCUMENTS 609837 3/1979 Switzerland .

OTHER PUBLICATIONS

Chemical Abstracts, 85:176885 m.
Chemical Abstracts, 94:139270x.
Chemical Abstracts, 63:11373h.

Schmidt, A. H., and Ried, W., Synthesis, (1978), pp. 869 to 880.
Paine, A. J., Tetrahedron Letters, (1984), 25, pp. 135 to 138.
Silvestri, G., et al., Gass. Chim. Itl., (1972), 102, pp. 818 to 821.
Uehara, A., and Tsuchiya, R., Sci. Rep. Kanazawa Univ., (1980), 25, p. 83.
Bellus, D., et al., Helv. Chim. Acta, (1978), 61, p. 1784.
Fabre. P. L., et al., Bull. Soc. Chim. Fr., (1988), p. 933.

*Primary Examiner*—James H. Reamer
*Attorney, Agent, or Firm*—Fisher, Christen & Sabol

[57] ABSTRACT

A process for the production of squaric acid by halogenation either of pure 3-acetoxy-2-cyclobuten-1-one or of a distillation residue of diketene production containing 3-acetoxy-2-cyclobuten-1-one to a cyclobutenone of formula:

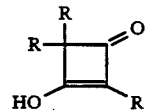

and then hydrolysis of these cyclobutenones to squaric acid. The halogenated cyclobutenones are intermediate products in the process.

9 Claims, No Drawings

PROCESS FOR THE PRODUCTION OF SQUARIC ACID

BACKGROUND OF THE INVENTION

1. Field Of The Invention

The invention relates to a new process for the production of squaric acid, in which squaric acid is isolated in high purity and with high yield, as well as to halogenated cyclobutenones as new intermediate products in the process.

2. Background Art

Squaric acid is an interesting intermediate product for the production of pharmaceutical agents, dyes (Angew. Chem., 20, (1966), p. 931) and herbicides (Swiss Patent No. 609,837). Various processes for the production of squaric acid are known from the literature.

Several of such processes start from hexachloro-1,3-butadiene, which is cyclized with sodium ethanolate to a chlorinated cyclobutene derivative. These intermediate products are hydrolyzed with sulfuric acid or other acids to squaric acid [Roedig, A., and Bernemann, P., Liebigs Ann. Chem., (1956), 600, p.1; Maahs, G., Liebigs Ann. Chem., (1965), 686, p. 55; Angew. Chemie, (1963), 75, p. 982; Uehara. A., and Tsuchiya, R., Sci. Rep. Kanazawa Univ., (1980), 25, p.83; Fan, R., et al., Chemical Abstracts, (1987), 106, 103798c]. Instead of sodium ethanolate, morpholine is also used [Maahs, G., and Hegenberg, P., Angew. Chemie, (1966), 78, p. 927; Schmidt, A. H., and Ried, W., Synthesis, (1978), p. 869; Gadek, T. R., et al., (1976), U.S. Pat. No. 4,104,308; Paine, A. J., Tetrahedron Letters, (1984), 25, p. 135]. The ring closure can also take place purely by thermal means [Mueller, W., (1976), German Patent No. 2,618,557; Schroeder, M., and Schaefer, W., (1976), German Patent No. 2,623,836; Maahs, G., and Rombusch, D., (1978), German OS 2,824,558; Rombusch, K., and Maahs. G., (1983), German Patent No. 3,314,431]. Disadvantages of all these processes are either modest yields or high expense (e.g., distillation with extreme reflux ratio) and the special safety measurements which are necessary in dealing with the carcinogenic feedstock hexachloro-1,3-butadiene.

According to another process [Bellus, D., et al., Helv. Chim. Acta, (1978), 61, p. 1784] squaric acid is obtained in 70 percent yield from the fungus metabolite moniliformin by bromation and hydrolysis. But moniliformin is present in nature only in small amounts and the known syntheses for it are expensive and produce only modest yields.

Another process, the electrochemical reductive tetramerization of carbon monoxide to squaric acid, requires a large expense for equipment and yields a product mixture from which the squaric acid can be isolated in pure form only with difficulty. [Silvestri, G., et al., Gazz. Chim. Itl., (1972), 102, p. 818; German OS 2,235,882; U.S. Pat. No. 4,461,681; U.S. Pat. No. 4,523,980; Fabre, P. L., et al., Bull. Soc. Chim. Fr., (1988), p. 933].

BROAD DESCRIPTION OF THE INVENTION

One of the objects of the invention is to provide a new synthesis of squaric acid, which starts from easily accessible feedstocks and produces squaric acid in good yield and purity. Other objects and advantages of the invention are set out herein or are obvious herefrom to one skilled in the art.

The objects and advantages of the invention are achieved by the invention process and invention compounds.

In the invention process, a distillation residue of (i) diketene production having a content of 3-acetoxy-2-cyclobuten-1-one, which is designated below as triketene, of the formula:

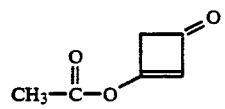

or (ii) pure triketene is either:

(a) in a first step, reacted by halogenation to a cyclobutenone of the formula:

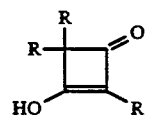

wherein R is identical in meaning and is a chlorine atom or bromine atom, this intermediate product is optionally isolated, and then, in a second step, this intermediate product is hydrolyzed to squaric acid; or (b) in a first step, converted by acid hydrolysis to a 1,3-cyclobutanedione, this first intermediate product is isolated, then, in a second step, the first intermediate product is reacted by halogenation to the cyclobutenone of formula II, this second intermediate product is optionally isolated and, in a third step, this second intermediate product is hydrolyzed to squaric acid.

Preferably a distillation residue from the diketene production with a triketene content of 5 to 60 percent by weight is used as the starting material.

The halogenation of pure triketene or triketene from the distillation residue of the diketene production, to the cyclobutenone according to formula II is suitably performed with 1 to 4 moles of bromine or chlorine, relative to 1 mole of starting material, preferably with 2.5 to 3.5 moles of bromine or chlorine, and especially with 2.5 to 3.5 moles of bromine. The reaction is usually performed at a temperature of 10° to 80° C., preferably 15° to 35° C.

After a reaction time of generally 10 to 180 minutes, either cyclobutenone according to formula II is obtained by the usual concentration by evaporation or the residue is hydrolyzed directly to squaric acid.

$C_1$–$C_4$ carboxylic acids, $C_1$–$C_4$ carboxylic acid esters, carboxylic acid anhydrides (best $C_1$–$C_4$) and chlorinated hydrocarbons (best $C_1$ or $C_2$) can be used as solvents for the halogenation reactions. As representatives of these solvents there can be used, for example, acetic acid, ethyl acetate, acetic anhydride, chloroform, methylene chloride and carbon tetrachloride—preferably ethyl acetate or acetic acid is used.

The acid hydrolysis of pure triketene or triketene from the distillation residue of the diketene production to 1,3-cyclobutanedione can be performed with aqueous acids, such as, excess formic acid or sulfuric acid. Excess aqueous formic acid is preferably used. The hydrolysis is usually performed at a temperature of 0° to 30° C., preferably 10° to 30° C. After a reaction time of generally 15 minutes to 24 hours, the 1,3-cyclobutanedione is worked up in the usual way, e.g., by extraction or recrystallization.

The second step, i.e., the halogenation of 1,3-cyclobutanedione, is performed with 1 to 5 moles of bromine or chlorine, relative to 1 mole of 1,3-cyclobutanedione, preferably with 2 to 4 moles of bromine or chlorine, and especially with 2.5 to 3.5 moles of bromine. The halogenation is usually performed at a temperature of 0° to 50° C., preferably of 0° to 20° C. After a reaction time of generally 30 minutes to 4 hours, the cyclobutenone, according to formula II, is obtained in good yield by concentration by evaporation or the residue is directly hydrolyzed to squaric acid. The same solvents as described above can be used as solvents in this step.

The cyclobutenones according to the formula:

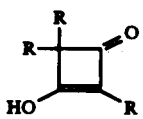

II wherein R is identical in meaning and is a chlorine atom or a bromine atom, are new and can be hydrolyzed to squaric acid, and the squaric acid can be isolated in good yield and purity. The preferred cyclobutenones of formula II are 2,4,4-tribromo-3-hydroxy-2-cyclobuten-1-one and 2,4,4-trichloro-3-hydroxy-2-cyclobuten-1-one. The hydrolysis to squaric acid can be performed with mineral acids, such as, sulfuric acid, hydrochloric acid, hydrobromic acid or phosphoric acid, with carboxylic acids, such as, aqueous formic acid or aqueous trifluoroacetic acid, with sulfonic acids, such as, aqueous methane sulfonic acid, or with water. Preferably excess mineral acids, such as, concentrated sulfuric acid or hydrochloric acid, are used. The hydrolysis is suitably performed at a temperature of 50° to 150° C., preferably at a temperature of 80° to 120° C. The hydrolysis to squaric acid with water is performed with reflux. After a reaction time of 2 to 48 hours, squaric acid is obtained in good yield.

DETAILED DESCRIPTION OF THE INVENTION

EXAMPLE 1

148 g of distillation residue of the diketene production having a triketene content of 15.5 percent by weight, was cooled to 10° C., and 17 ml of this residue was added in a thin-layer evaporator per hour at a pressure of 0.1 to 0.3 mbar. In this case, 4 g of brownish crystals with a 97 percent triketene content and 20 g of yellow liquid with a 51.5 percent triketene content were separated. The distillation residue was freed from diketene and other highly volatile impurities at a temperature of 20° to 40° C. and a pressure of 0.2 mbar for 20 minutes, then dissolved in diethyl ether (50 ml), cooled to −60° C. and filtered. The residue was washed with −60° C. cold diethyl ether (10 ml) and dried using suction. The 11.7 g of brownish crystals was sublimated at a temperature of 30° C. and a pressure of 0.1 mbar. The sublimation yielded 10.5 g of colorless triketene crystals, corresponding to a yield of 46 percent, relative to the triketene contained in the diketene resin. The triketene had a melting point of 34° C.

EXAMPLE 2

Production of 2,4,4-tribromo-3-hydroxy-2-cyclobuten-1-one 7 4.84 g of bromine (30 mmol), dissolved in ethyl acetate (10 ml), was instilled in 1.26 g (10 mmol) of triketene, dissolved in ethyl acetate (10 ml), within 20 minutes with stirring. The reaction temperature was kept between 22° and 30° C. After another hour of stirring at room temperature, the orange solution was concentrated by evaporation on a rotary evaporator. After concentration by evaporation, 3.07 g of product, corresponding to a yield of 96 percent relative to the triketene used, was obtained. Data for the product was: Melting point: 163° C. (decomposition)
$^{13}$H-NMR (d$_7$-DMF, 300 MHz, δ in ppm): 11.2, bs.
$^1$H-NMR(d$_7$-DMF, 300 MHz, δ in ppm): 71, s; 178, s; 209, s; 221, s.

EXAMPLE 3

Production of 1,3-cyclobutanedione 14 g of triketene (content 95 percent, 105 mmol) was added by portions at 10° C. to a mixture of 140 g of formic acid and 4.6 g of water (256 mmol). It was concentrated by evaporation after 4 hours. The brown residue was suspended in diethyl ether (20 ml), filtered off and washed with diethyl ether (5 ml). After drying, 8.8 g of light brown crystals remained with a melting point of 118° to 119° C. (decomposition) and a content of 97 percent 1,3-cyclobutanedione, which corresponds to a yield of 96 percent, relative to triketene.

EXAMPLE 4

Production of 2,4,4-trichloro-3-hydroxy-2-cyclobuten-1-one 0.84 g (10 mmol) of 1,3-cyclobutanedione was suspended in carbon tetrachloride (10 ml). 2.3 g (32 mmol) of chlorine was introduced with stirring in 45 minutes at 2° to 4° C. After completion of the addition of the chlorine, the yellow suspension was stirred for 1 more hour at 4° to 9° C. By concentration by evaporation on a rotary evaporator, 1.7 g of product, corresponding to a yield of 90 percent, relative to the 1,3-cyclobutanedione used, was obtained. Data for the product was:
Melting point: 156° to 159° C. (decomposition)
$^1$H-NMR (d$_7$-DMF, 300 MHz, δ in ppm): 9, 8, s.

EXAMPLE 5

Production of squaric acid by hydrolysis with sulfuric acid (a) Starting from 2,4,4-Tribromo-3-Hydroxy-2-Cyclobuten-1-One Concentrated sulfuric acid (99%, 5 ml) was added to 3.07 g (9.6 mmol) of 2,4,4-tribromo-3-hydroxy-2-cyclobuten-1-one. This suspension was stirred for 15 hours at 100° C., then cooled and filtered. The residue was washed 3 times with acetone (1 ml each) and then dried for 4 hours at 50° C. and 40 mbars. 1.03 g of such crystals with a content of 95 percent squaric acid was obtained, corresponding to 0.97 g (8.5 mmol) of squaric acid and a yield of 85 percent, relative to the triketene used.

(b) Starting from 2,4,4-Trichloro-3-hydroxy-2-Cyclobuten-2-One

Concentrated sulfuric acid (99%, 4 ml) and water (0.5 ml) were added to 1.7 g (9 mmol) of 2,4,4-trichloro-3-hydroxy-2-cyclobuten-1-one. The suspension was stirred for 15 hours at 80° C., cooled and filtered. The residue was washed 3 times with acetone (2 ml each)

and then dried at 50° C. and 40 mbars for 15 hours. 0.71 g of gray solid with a squaric acid content of 93 percent was obtained, corresponding to 0.66 g (5.8 mmol) of pure squaric acid and a yield of 58 percent, relative to 1,3-cyclobutanedione.

EXAMPLE 6

Production of Squaric Acid by Hydrolysis with Water 10 ml of water was added to 1.30 g (4.1 mmol) of 2,4,4- tribromo-3-hydroxy-2-cyclobuten-1-one. The yellowish solution was refluxed for 14 hours, cooled to 5° C. and filtered. The residue was washed twice with 0.5 ml of water each and then dried at 50° C. and 40 mbars for 16 hours. 0.344 g of gray crystals was obtained, which contained 96 percent squaric acid, which corresponds to 0.330 g (2.9 mmol) of squaric acid and a yield of 70 percent, relative to the triketene used.

EXAMPLE 7

Production of Squaric Acid by Hudrolysis with Other Acids

Analogously to Example 5a, squaric acid was produced by hydrolysis of 0.50 g (1.6 mmol) each of 2,4,4- tribromo-3-hydroxy-2-cyclobuten-1-one. The results are:

| Aqueous acid Name | Content | g | Yield of squaric acid rel. to triketene used |
|---|---|---|---|
| hydrochloric | 36% | 1.8 | 53% |
| phosphoric | 84% | 3.4 | 52% |
| hydrobromic | 48% | 3.0 | 48% |
| trifluoroacetic | 96% | 3.0 | 84%* |
| formic | 98% | 2.4 | 77%* |
| methane sulfonic | 92% | 1.2 | 60% |

Note: *in solution

What is claimed is:

1. Process for the production of squaric acid, comprising:
   (a) treating a composition which is (i) a distillation residue of diketene production, which contains 3-acetoxy -2-cyclobuten-1-one of formula:

or (ii) pure 3-acetoxy-2-cyclobutene-1-one, in a first step, reacting said composition by chlorination or bromination to a cyclobutenone of formula:

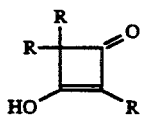

wherien R is idnetical in meansing and each R is chlorine or bromine, respectivley, said 3-acetoxy-2-cyclobuten -1-one being performed at a temperature of 10° to 80° C., optionally isolating the cyclobutenone of formula II; and
   (b), then, in a second step, hydrolyzing the cyclobutenone of formula II to squaric acid of formula:

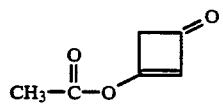

the hydrolysis to squaric acid being performed at a temperature of 50° to 150° C.

2. Process according to claim 1 wherein a distillation residue of diketene production having a 3-acetoxy-2-cyclobuten -1-one content of 5 to 60 percent by weight, is used as said composition.

3. Process according to claim 1 wherien the hydrolysis to squaric acid is performed with a mineral acid, a sulfonic acid, a carboxylic acid or water.

4. Process according to claim 3 wherien the hydrolysis to squaric acid is performed with concentrated sulfuric acid.

5. Process for the production of squaric acid, comprising:
   (a) treating a composition which is (i) a distillation residue of diketene production, which contains 3-acetoxy -2-cyclobuten-1-one of formula:

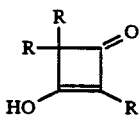

or (ii) pure 3-acetoxy-2-cyclobuten-1-one, in a first step, converting siad composition by acid hydrolysis to the corresponding 1,3-cyclobutanedione, said acid hydrolysis being performed at a temperature of 0° to 30° C., and isolating the corresponding 1,3-cyclobutanedione;
   (b) then, in a second step, reacting the corresponding 1,3-cyclobutanedione by chlorination or bromination to a cyclobutenone of formula:

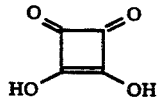

wherein R is identical in meansing and each R is chlorine or bromine, respectively, said chlorination or bromination of 1,3-cyclobutanedione being performed at a temperature of 0° to 50° C., optionally isolating the cyclobutenone of formula II; and
   (c) then, in a third step, hydrolyzing the cyclobutenone of formula II to squaric acid of formula:

the hydrolysis to squaric acid being performed at a temperature of 50° to 150° C.

6. Process according to claim 5 wherien a distillation residue of diketene production having a 3-acetoxy -2-cyclobuten-1-one content of 5 to 60 percent by weight, is used as said composition.

7. Process according to claim 5 wherein the acid hydrolysis to 1,3-cyclobutanedione is performed with aqueous formic acid or aqueous sulfuric acid.

8. Process accoridng to claim 5 wherien the hydrolysis to squaric acid is performed with a mineral acid, a sulfonic acid, a carboxylic acid or water.

9. Process according to claim 8 wherien the hydrolysis to squaric acid is performed with concentrated sulfuric acid.